(12) United States Patent
Fox et al.

(10) Patent No.: US 12,340,650 B2
(45) Date of Patent: Jun. 24, 2025

(54) ROBOTIC DEVICE FOR DISTRIBUTING DESIGNATED ITEMS

(71) Applicant: XTEND AI Inc., Middleburg, FL (US)

(72) Inventors: Harry Fox, Jerusalem (IL); David Azoulay, Jerusalem (IL); Sergh Sapojnikov, Ashkelon (IL); Andrew C. Gorelick, Ashkelon (IL)

( * ) Notice: Subject to any disclaimer, the term of this patent is extended or adjusted under 35 U.S.C. 154(b) by 0 days.

(21) Appl. No.: 18/476,344

(22) Filed: Sep. 28, 2023

(65) Prior Publication Data

US 2024/0112518 A1 Apr. 4, 2024

Related U.S. Application Data

(60) Provisional application No. 63/585,616, filed on Sep. 27, 2023, provisional application No. 63/480,975, (Continued)

(51) Int. Cl.
*G07F 17/00* (2006.01)
(52) U.S. Cl.
CPC .................. *G07F 17/0092* (2013.01)
(58) Field of Classification Search
None
See application file for complete search history.

(56) References Cited

U.S. PATENT DOCUMENTS 9,489,490 B1   11/2016   Theobald
10,207,296 B2   2/2019   Garcia
(Continued)

FOREIGN PATENT DOCUMENTS

CN   111267117 A   6/2020
CN   111993978 A   11/2020
(Continued)

OTHER PUBLICATIONS

International Search Report and PCT Written Opinion for Application No. PCT/US2023/075296 mailed Mar. 8, 2024.
(Continued)

*Primary Examiner* — Thomas E Worden
*Assistant Examiner* — Bryant Tang
(74) *Attorney, Agent, or Firm* — JMB DAVIS BEN-DAVID

(57) ABSTRACT

A robotic device for distributing designated items to persons includes a motion unit to autonomously move the robotic device through a premise, storage for designated items, an item dispenser to dispense from the storage, memory modules containing recognition scans and payment information of persons located within the premise and information of the designated items. The memory modules contain secondary recognition scans of persons located within the premise, recognition scanners, secondary recognition scanners, an additional scanner by an exit tube, a control unit in communication with the motion unit, the recognition scanners, the memory and the item dispenser and where the control unit directs the motion unit to move the robotic device within the premise, upon encountering a purchaser who selects a designated item, directs the recognition scanners to scan payment details of the purchaser and compares images from the recognition scanners to stored recognitions scans to verify payment.

12 Claims, 16 Drawing Sheets

Related U.S. Application Data filed on Jan. 22, 2023, provisional application No. 63/378,073, filed on Oct. 2, 2022.

(56) References Cited

U.S. PATENT DOCUMENTS

| | | | |
|---|---|---|---|
| 11,203,120 | B1 | 12/2021 | Hill |
| 11,565,425 | B2 | 1/2023 | Fox |
| 12,019,442 | B1 * | 6/2024 | Ebrahimi Afrouzi ........................ G05D 1/0088 |
| 2001/0056311 | A1 | 12/2001 | Valerino, Sr. |
| 2004/0019406 | A1 | 1/2004 | Wang |
| 2005/0021182 | A1 | 1/2005 | Wang |
| 2008/0262649 | A1 * | 10/2008 | Allinson .................. G07F 11/62 700/235 |
| 2010/0206651 | A1 | 8/2010 | Nagasaka |
| 2015/0134106 | A1 | 5/2015 | Boyer |
| 2018/0154514 | A1 | 6/2018 | Angle |
| 2018/0333860 | A1 | 11/2018 | Jamriska |
| 2019/0381661 | A1 | 12/2019 | Taira |
| 2020/0061839 | A1 | 2/2020 | Deyle et al. |
| 2020/0202288 | A1 * | 6/2020 | Buibas .................. G06T 19/003 |
| 2020/0361715 | A1 | 11/2020 | Meier |
| 2020/0411154 | A1 | 12/2020 | Lee |
| 2021/0252712 | A1 | 8/2021 | Patrick |
| 2021/0354945 | A1 | 11/2021 | Deng |
| 2022/0126452 | A1 | 4/2022 | Pennington |
| 2022/0347859 | A1 | 11/2022 | Fox et al. |

FOREIGN PATENT DOCUMENTS

| | | | |
|---|---|---|---|
| CN | 112207838 | A * | 1/2021 |
| CN | 112276967 | A | 1/2021 |
| CN | 215789886 | U | 2/2022 |
| GB | 2598037 | A | 2/2022 |
| WO | 2014168955 | A1 | 10/2014 |
| WO | 2016086806 | A1 | 6/2016 |

OTHER PUBLICATIONS

Combined Search and Examination Report for corresponding GB application 2300974.9 mailed on Mar. 15, 2023.

Jarvis, "Multimodal Robot/Human Interaction in an Assistive Technology Context", 2009, IEEE, p. 212-218.

Suthakorn et al., "A Robotic Library System for an Off-Site Shelving Facility", 2002, IEEE, p. 3589-3594.

Miseikis et al., "Lio-A Personal Robot Assistant for Human-Robot Interaction and Care Applications", 2020, IEEE, p. 5339-5346.

Choi et al., "Robotic Laboratory Automation Platform Based on Mobile Agents for Flexible Clinical Tests", 2010, IEEE, p. 186-191.

Lima et al., "Robotic Telemedicine for Mental Health: A Multimodal Approach to Improve Human-Robot Engagement", Frontiers in Robotics and AI 8 (2021): 618866, Mar. 18, 2021, Retrieved on Jul. 19, 2022 from <https://www.frontiersin.org/articles/10.3389/frobt.2021.618866/full>.

West et al., "Machine Vision in Practice", 1983, IEEE, p. 794-801.

Illman et al., "Statistical Recognition of Motion Patterns", 2002, IEEE, p. 1259-1269.

Rajput et al., "Alternative Product Label Reading and Speech Conversion: An Aid for Blind Person", 2017, IEEE, p. 1-6.

Zhuang et al., "3-D-Laser-Based Scene Measurement and Place Recognition for Mobile Robots in Dynamic Indoor Environments", 2012, IEEE, p. 438-450.

* cited by examiner

ROBOTIC DEVICE FOR DISTRIBUTING DESIGNATED ITEMS

CROSS REFERENCE TO RELATED APPLICATIONS

This application claims priority from U.S. provisional patent applications 63/378,073, filed Oct. 2, 2022, 63/480,975, filed Jan. 22, 2023 and 63/585,616 filed Sep. 27, 2023 all of which are incorporated herein by reference.

FIELD OF THE INVENTION

This invention pertains to the field of robotics, and, in particular, to a robotic device for distributing designated items.

BACKGROUND OF THE INVENTION

There are stand-alone stationary devices in in the market that issue alerts that it is time to take medication. These cue someone to go and take the medication. Also very common are boxes or containers with marked compartments, so someone knows which medicine to take at a particular time.

Stand-alone automatic pill dispensers exist in the market. By activating a program and then pushing a button, the required medicine can be accessed. Some of these dispensers automatically send alerts about the need to take a specified medication. Further, some are connected to the Internet, or a local network, so they can be remotely activated to dispense medication.

Pria has a mobile app that alerts you when it is time to take a prescribed medication. https://www.okpria.com/How-it-works. The user then goes to the Pria pill wheel and is recognized by facial recognition and the medication can then be received from the pill wheel.

SUMMARY OF THE PRESENT INVENTION

To achieve these and other objects, the herein robotic device can efficiently and effectively distribute items, like a mobile vending machine. It has particular application in hotels, medical centers, nursing facilities, assisted living centers and similar facilities, where a myriad of people need to be able to obtain various items in a simple, efficient manner.

Therefore, to achieve these and other objects, the herein disclosed invention is a robotic device for distributing designated items to persons, comprising: a motion unit to autonomously move said robotic device through a premise; storage means comprising multiple compartments for containing designated items; an item dispenser to dispense items from the storage means; an external or internal memory module containing recognition scans and payment information of persons located within said premise, and substantive information of said designated items; recognition scanners; a control unit in electronic communication with the motion unit, the recognition scanners, the memory and the item dispenser; and, where, the control unit directs the motion unit to move the robotic device within the premise, upon encountering a purchaser and the purchaser selects a designated item directs the recognition scanners to scan payment details of the purchaser, and compares images from the recognition scanners to recognitions scans in the memory to verify payment; and, where, upon verifying payment, the control unit directs said item dispenser to dispense the designated item.

Preferably, the item dispenser of the robotic device comprises: a movable vacuum tube, a controlled vacuum, a mobile arm for controlled movement of the vacuum tube and an exit tube, where the control unit directs the storage means to rotate until a compartment for the designated item is in alignment with the vacuum tube, activates the controlled vacuum to suck and hold the designated item into the vacuum tube, directs the mobile arm to move the vacuum tube until it aligns with the exit tube, and deactivates the controlled vacuum causing the designated item to fall through the exit tube.

The payment details may include a smartphone payment app, a credit card with an electronic payment chip, or a QR (quick response) image.

In one embodiment, the device further comprising secondary recognition scanners; and, the memory module further containing secondary recognition scans of persons located within the premise; and, where, prior to dispensing the designated item, the control unit directs the secondary recognition scanners to scan the person, and compares images from the secondary recognition scanners to secondary recognitions in the memory to confirm the person is the person associated with the payment information. These secondary recognition scanners may be magnetic code readers, fingerprint scanners or eye scanners or facial scanners or optical scanners and said secondary recognition scans of persons located within said memory being magnetic codes, fingerprint scans or eye scans or facial scans or optical scans.

The item dispenser may further comprise substantive scanners and the memory module further containing substantive scans of the designated items; and, where, prior to dispensing the designated item, the control unit directs the substantive scanners to scan the designated item, and compares scans from the substantive scanners to substantive scans in the memory to confirm the designated item is the correct designated item for the person.

For security and safety purposes in some embodiments, the storage means further comprising supplemental recognition scanners; and, the memory module further containing supplemental recognition scans of persons authorized to add items to the storage means; and, where, prior to adding items to the storage means, the control unit directs said supplemental scanners to scan persons attempting to add items to the storage means, and compares scans from the supplemental scanners to supplemental scans in the memory to confirm said persons attempting to add items to the storage means are authorized to add items to the storage means.

Another embodiment is a robot device for distributing items, the robot having multiple storage units to store at least one item for distribution, a control unit to determine the distribution according to facial recognition of a user requesting an item or receipt of payment and payment verification for the item; and a dispensing unit to dispense the at least one item from one of the multiple storage units according to the control unit.

The payment is via a payment terminal embodied with the robot device or from an external server in communication with the control unit of the robot device.

The distribution is according to stock levels of the at least one item and where the control unit monitors the stock levels and the robot device refills stock according to instructions from the control unit based on stock levels.

Another embodiment is a robot for distributing items, the robot includes multiple storage units to store items for distribution; and a control unit to receive requests from at least two users for items and to determine distribution of the items, the control unit includes a task manager to coordinate handling the requests, where the robot device moves autonomously to the at least two users.

The task manager uses at least one of FIFO (first in first out) and distance to travel to determine the distribution.

The robot further includes a payment module to receive and verify payment for the items when payment is required.

Another embodiment of the invention is a robot, the robot includes a control unit to enable the robot to autonomously move through a premise with customers; multiple storage units to store items for sale; a payment terminal to receive payment for at least one item from a customer of the customers; a payment module to verify the payment; and a dispensing unit to dispense the at least one item according to the payment module.

The payment module further includes a user profile system to recognize the customer for automatic payment from a least one of: scanning of a room key, scanning of a QR code on a mobile phone, NFC or Wi-Fi transfer from a mobile phone and facial recognition.

Another embodiment of the invention is a robot including multiple storage units to store items; and a control unit to receive at least one request from a user for at least one item for distribution, the control unit includes a stock control handler to determine stock levels for the at least one item and to instruct the robot to refill stock from a stock room when required; and an item dispenser to dispense the at least one item if it is in stock; where the robot device moves autonomously to the user and to the stock room.

BRIEF DESCRIPTION OF THE DRAWINGS

For a better understanding of the invention and to show how it may be carried into effect, reference will now be made, purely by way of example, to the accompanying Figures, wherewith it is stressed that the particulars shown are by way of example and for purposes of illustrative discussion of the preferred embodiments of the present invention only, and are presented in the cause of providing what is believed to be the most useful and readily understood description of the principles and conceptual aspects of the invention.

DETAILED DESCRIPTION OF THE PRESENT INVENTION

Figure 1:
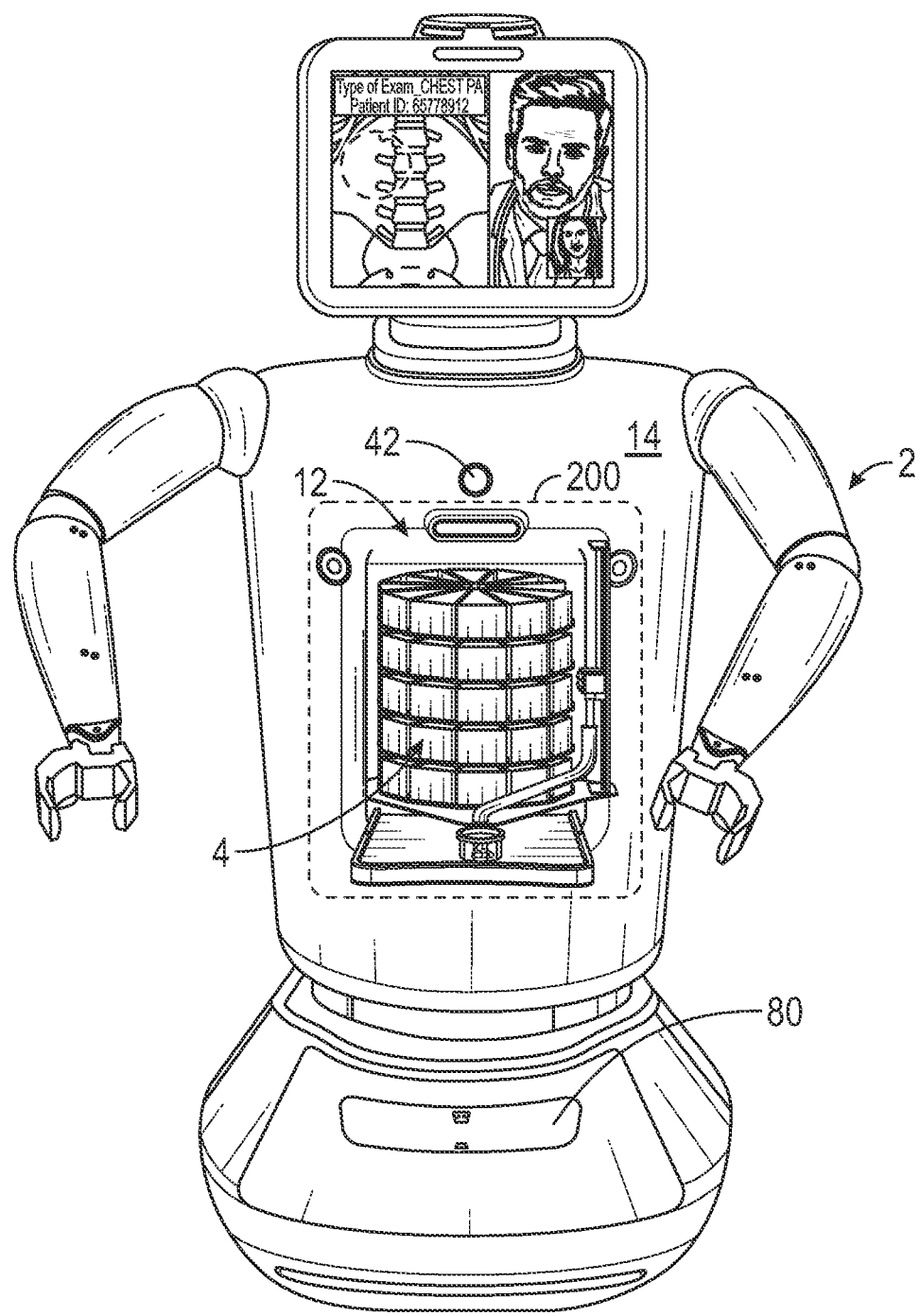
FIG. 1 is a front view of a robotic device containing a medication dispenser; constructed and operative in accordance with the present invention.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Applicants have realized that the standalone and mobile robot dispensing devices as described herein above and as described in US Patent Application No. 11,565,425 entitled "Robotic Device For Distributing Designated Items," granted Jan. 31, 2023, commonly owned by Applicant and incorporated herein by reference, could be improved to provide a robot that can autonomously move to make deliveries and even deliver vending machine products for pay. An example may be a hotel setting where the robot could deliver clean towels and shampoo or take specific orders. It could do this to accomplish the goal of alleviating the need for full-time staff on each floor of a hotel. It may allow staff members to accomplish more in managing amenities, refills, and restocks with greater ease. Such a robot could go to each hotel guest or room individually, deliver items when summoned and keep a direct account of its inventory. Keeping direct account of the inventory in combination with autonomous movement allows the robot to know when a refill is required and return to a restock room when it is required. Therefore, the hotel staff could have a singular point of operation (possibly per floor or with the use of smart elevators per building or complex) and not need to run around. In an alternative embodiment, robot 5 may be used in a hospital setting dispensing items such as medication, toiletries etc. or may be used as a vending machine for patients and visitors to buy snacks.

The robot may include a stock control system to keep a tally of its stock and know when to refill and may also be coupled with a payment system that may allow for the purchase of an item using a method of payment. It will also be appreciated, as described in the hotel example above, that the robot may also be in communication with a larger management system such as a hotel concierge system which may charge a purchased item to a guest hotel room. The robot may also have some form of task management system in order to handle multiple concurrent requests. The robot may need to coordinate between visiting rooms, receiving requests and restocking items that have run out.

The robot may include different modes to handle items distributed for free (such as hotel towels and shampoos), items bought using a payment method (such as cold drinks and snacks) and items that need to be charged by an external source such as a hotel management system.

According to the broadest definition of the invention, it pertains to a robotic device for distributing designated items to designated persons, comprising:
  Means for autonomously moving said robotic device through a premise;
  Storage means including multiple compartments for containing designated items;
  Means for dispensing items from said storage means;
  An external or internal memory module containing optical recognition scans and personal information of persons located within said premise, and substantive information of said designated items;
  Optical recognition scanners;
  A control unit in electronic communication with said means for autonomously moving, said optical recognition scanners, said memory and said means for dispensing as well as handling stock control, payments and task management and,
  Wherein, the control unit directs said means for autonomously moving to move said robotic device within the premise, directs the optical recognition scanners to scan persons as they are encountered, compares images from said optical recognition scanners to optical recognitions in the memory to identify the person; and,
  Wherein, upon identifying said person, the control unit searches the personal information of the person in the memory and identifies designated items specified for the person, and then directs the means for dispensing to dispense said designated item to the person.

In an embodiment of the invention, the designated items are pharmaceutical products and the robot is preferably used to distribute medication to residents and patents in hospitals, medical centers and elder care facilities.

According to the invention, the robot autonomously moves the premises. When it encounters a person, it takes an optical scan of that person. It searches to see if that person is in memory. If there is a match, the memory identifies the medication for that person.

The means for dispensing can be any suitable electromechanical device. In one embodiment, it involves a movable vacuum tube. The storage means rotates—or otherwise moves, until the compartment for the designated medicine is in alignment with a vacuum tube attached to a mobile arm. By means of a controlled vacuum, the medicine is sucked into a vacuum tube and held. The mobile arm then moves vacuum tube until it aligns with an exit tube. At this point, the vacuum is deactivated and the medicine falls through the exit tube.

At the bottom of the exit tube, a cup [or other catching element] receives the medicine. The designated patient may then take the cup with the medicine.

According to a preferred embodiment, the device may additionally include secondary recognition scanners; and, the memory module further containing secondary recognition scans of persons located within the premise; and, where, prior to dispensing the designated item, the control unit directs the secondary recognition scanners to scan the person, compares images from the secondary recognition scanners to secondary recognitions in the memory to confirm said person is the correct person to receive the designated item.

To ensure that the patient taking the medicine is in fact the correct person for that medicine, additional scanners may be provided at the point where the cup and medicine are located. This way there is additional protection to prevent the wrong person from getting the medicine.

For additional protection, said means for dispensing further comprising substantive scanners and said memory module further containing substantive scans of said designated items; and, where, prior to dispensing said designated item, said control unit directs said substantive scanners to scan said designated item, compares scans from said substantive scanners to substantive scans in said memory to confirm said designated item is the correct designated item for said person.

By this means, it assures that the correct medicine was selected.

It may be appreciated that while the preferred use is for the distribution of medicine, any objects may be distributed to any collection of people. For example, designated toys can be delivered to designated children.

The storage means including multiple compartments for containing designated items; and the means for dispensing items from said storage means may preferably be made as a single unitary unit. In any suitable manner it may be mounted on the robot. One possible way to mount them would be to affix them to a drawer or shelf that slides into and out of the robot.

In a preferred embodiment, the robotic medication dispenser can store and automatically dispense up to 60 different medications, including:
  PRN Medications.
  Controlled substances.
  Multiple Security Protocols may be incorporated into the robotic device,
  Face Recognition.
  Bar Code Scanning.
  Fingerprint Verification.
  Estimated Module Dimensions: 370×270×590 mm.
  Capacity: 55 pill cartridge compartments.
  Pill Size: Supports any pill size and shape.
  User Support: Virtually unlimited users per device.

Regulations: The materials meet the requirements of FDA.

It will be appreciated that when distributing items larger than pills, the distribution mechanism may vary according to the size and weight of product being distributed. In this scenario larger tubes or hatch system may be required. For example towels may be distributed onto a surface and not into a cup.

Figure 2:
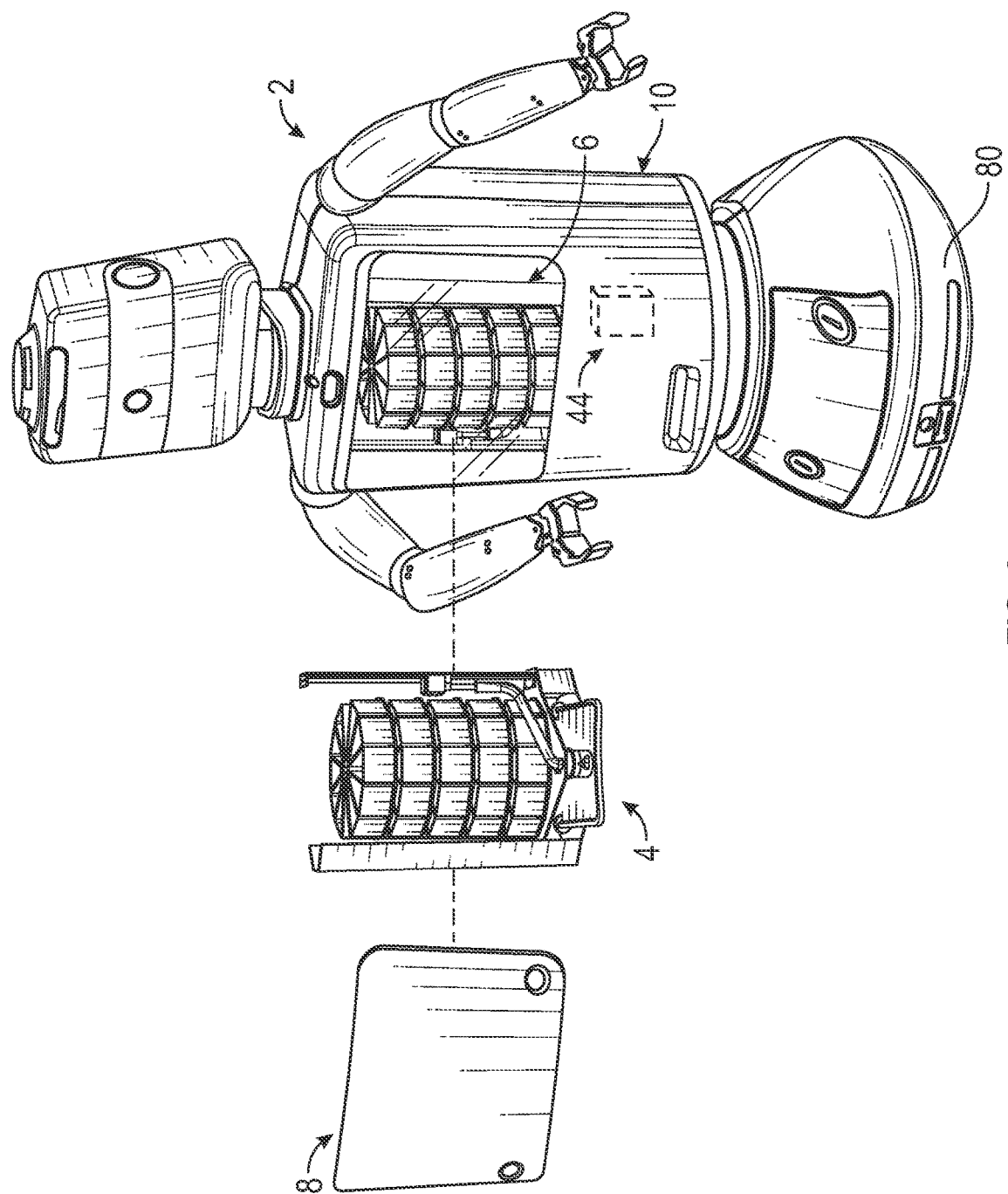
FIG. 2 is a rear perspective exploded view showing the medication dispenser inserted into the robotic device constructed and operative in accordance with the present invention.
Figure 3:
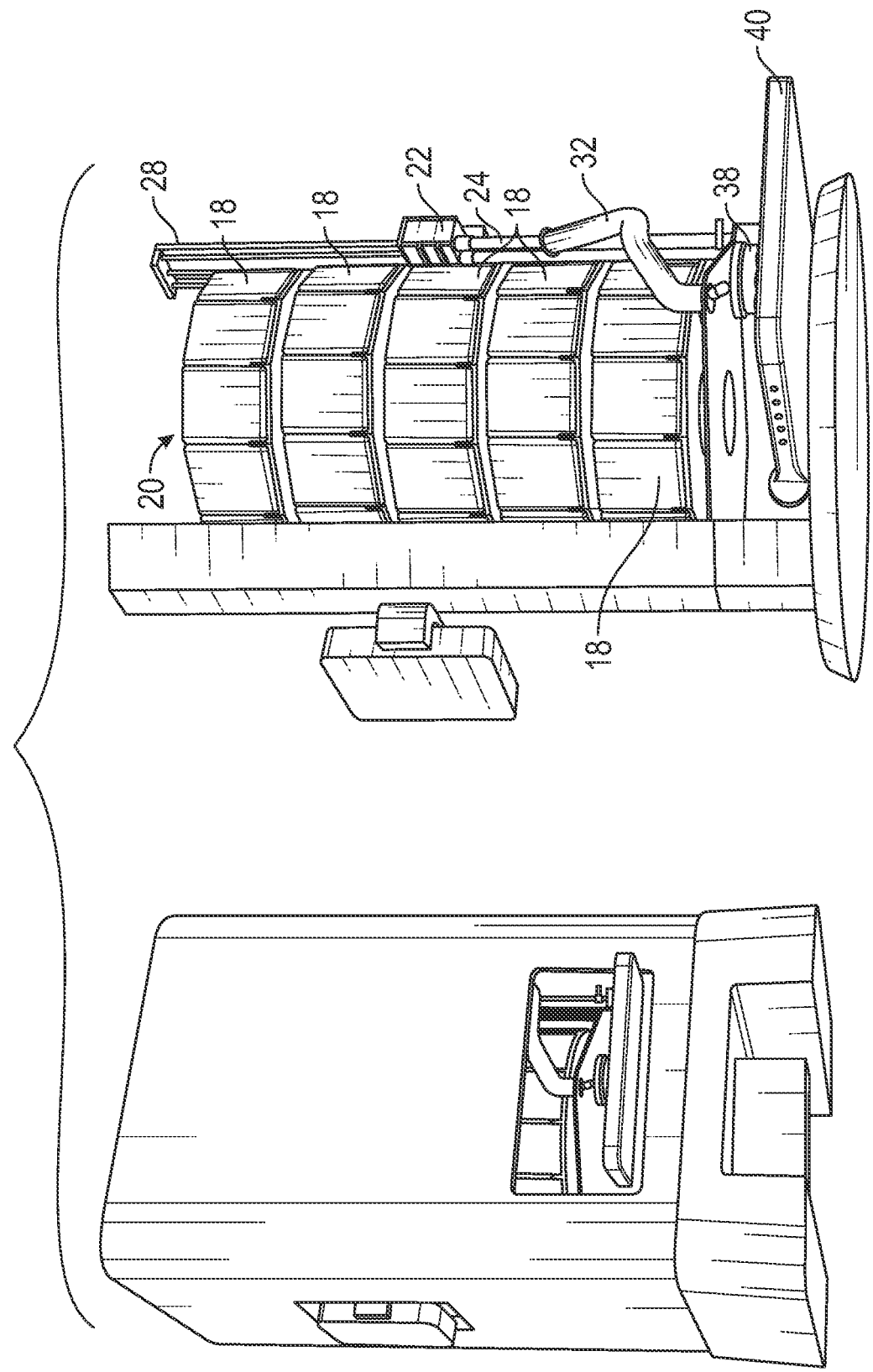
FIG. 3 is an enlarged perspective view, showing the medication dispenser and its housing, constructed and operative in accordance with the present invention.

Reference is now made to FIG. 1, FIG. 2 and FIG. 3 which illustrate an autonomous robot 2 used as a mobile delivery service/vending machine according to an embodiment of the present invention. Any standard or conventional robot may be used to house a dispensing unit 200 which comprises dispenser 4 within an internal cavity 6. A cover 8 on the rear surface 10 may enclose dispenser 4 to prevent damage or tampering. An opening 12 in front torso 14 permits access to the selected medication. If desired, the front torso 14 can have an opening 12 to expose all or most of the dispenser (FIG. 1) or closed to seal the dispenser inside the robot except for an exit opening 16 (FIG. 3). Robot 2 may also include at least one scanner 42 and a control unit 80 to provide means for autonomously moving robot 2 through a premise using an AI process that allows robot 2 to direct itself through the premises without external guidance.

In a preferred embodiment, storage means includes multiple compartments 18 for containing designated items as constituted by the dispenser 4 as shown in FIG. 3 to which reference is now made. As shown dispenser 4 has any suitable shape and size. The specific shape and size are dependent on the number of medications that are to be contained within. In a preferred embodiment, dispenser 4 can be multi-level carousel 20 with compartments 18 and rotating about a central rod (not shown).

Dispensing unit 200 may be constructed as a movable vacuum tube 24. Motor 29 moves vacuum tube 24 vertically along a track running alongside the dispenser. When a medication and its location is identified, vacuum motor 29 is moved to the vertical level corresponding to the compartment in which the medication is contained. Then, dispenser 4 is rotated until the compartment containing the medication is in alignment with vacuum tube 24. The vacuum is activated to pull the medication out of the compartment and to hold it in vacuum tube 24. By means of motor 29, vacuum tube 24 is moved until it is in alignment with the exit tube. The vacuum is deactivated and the medication falls through exit tube 32 to be accessible to the recipient.

Figure 4:
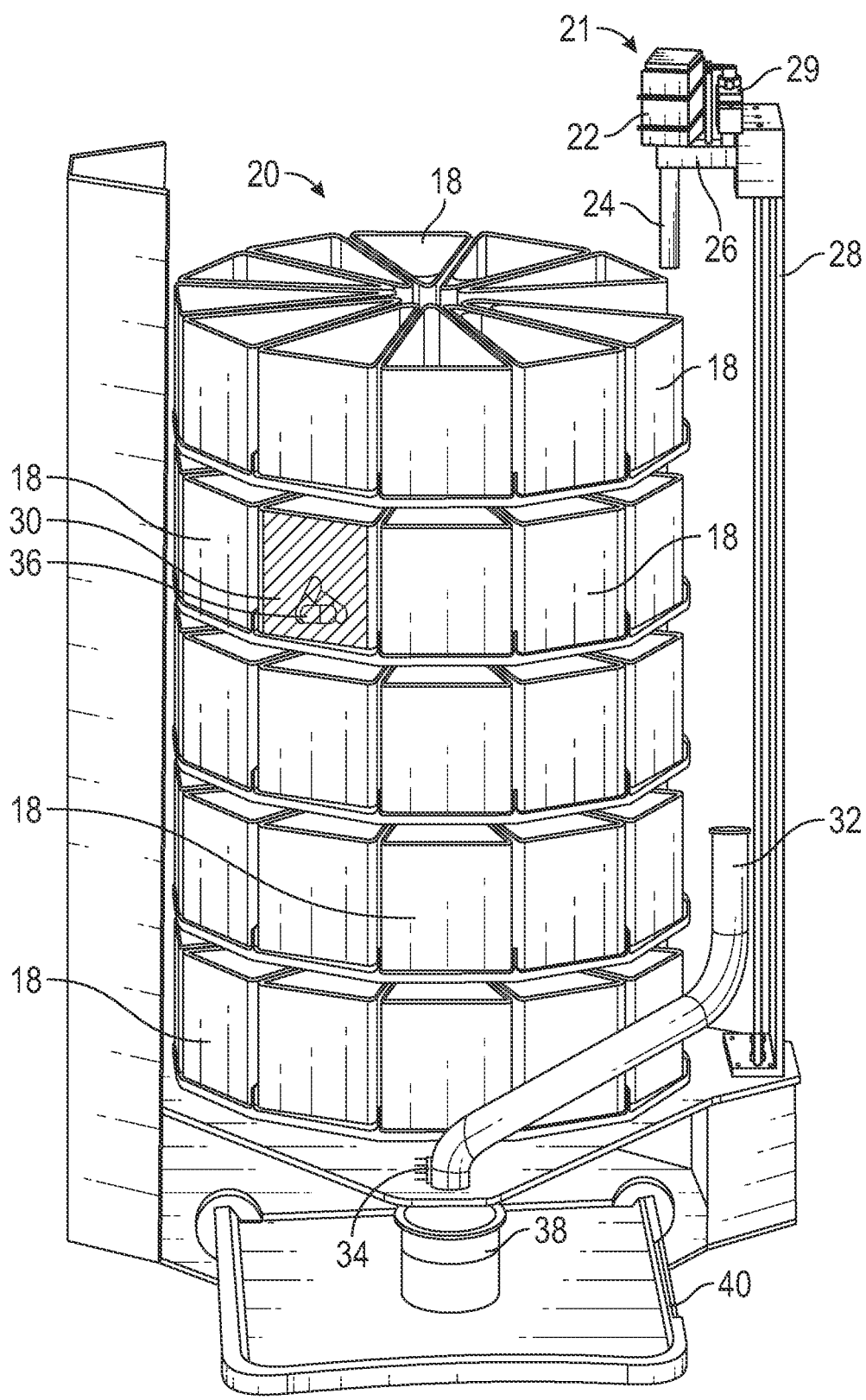
FIG. 4 is a front perspective of the medication dispenser and showing all the elements of the extraction device, constructed and operative in accordance with the present invention.

As shown in FIG. 4 to which reference is now made, the means for dispensing includes an extraction device 21 including a vacuum pump 22 and an accompanying vacuum tube 24. They are supported on platform 26 that travels along guide rail 28. Motor 29 energizes the vacuum pump 22 during operation. When not in use, the extraction device rests near the top of guide rail 28 above carousel 20.

In a preferred embodiment, the multi-level carousel 20 has five levels with fifty-five compartments 18—eleven compartments per level. One vertical column of compartments is empty with no compartments and is a clear unobstructed column as hereinafter described.

Figure 5:
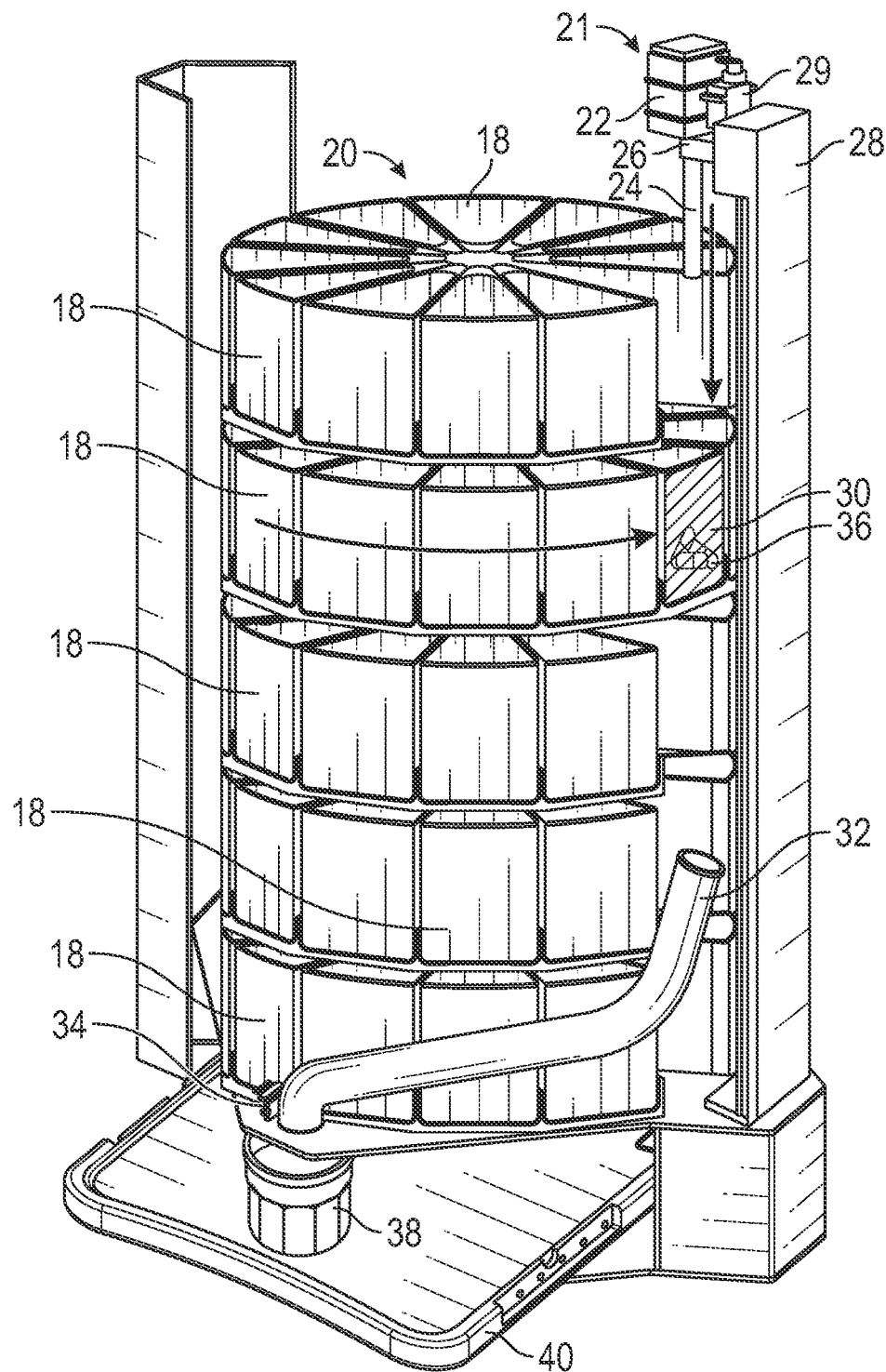
FIG. 5 is a front perspective of the medication dispenser and showing all the elements of the extraction device and the compartment with the medication constructed and operative in accordance with the present invention.
Figure 6:
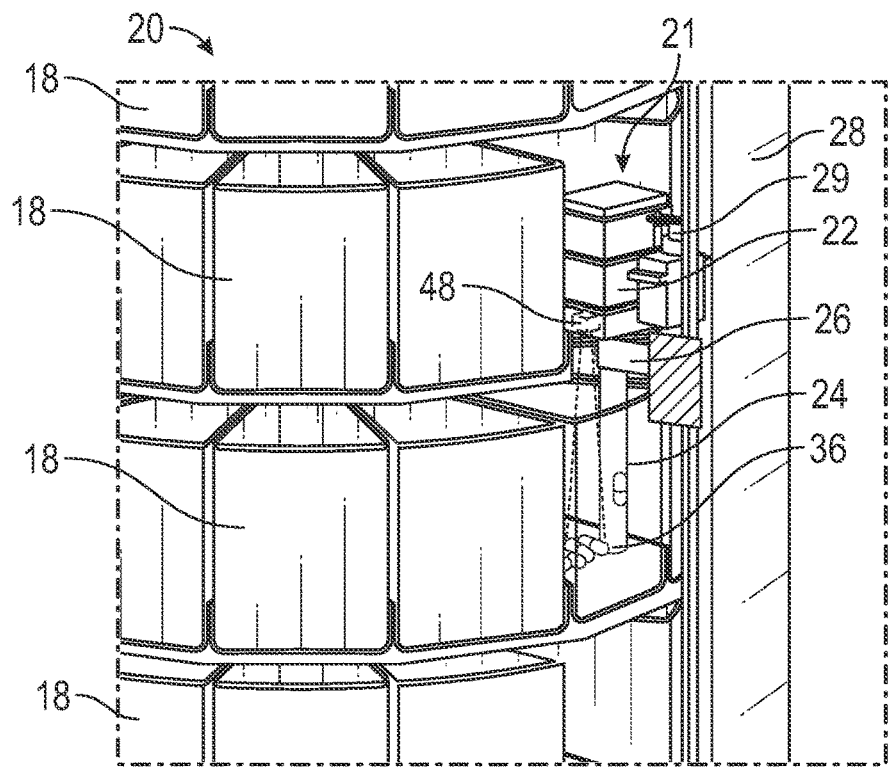
FIG. 6 is an enlarged front view of a portion of the medication dispenser and showing the extraction device coming into engagement with the compartment with the medication, constructed and operative in accordance with the present invention.
Figure 7:
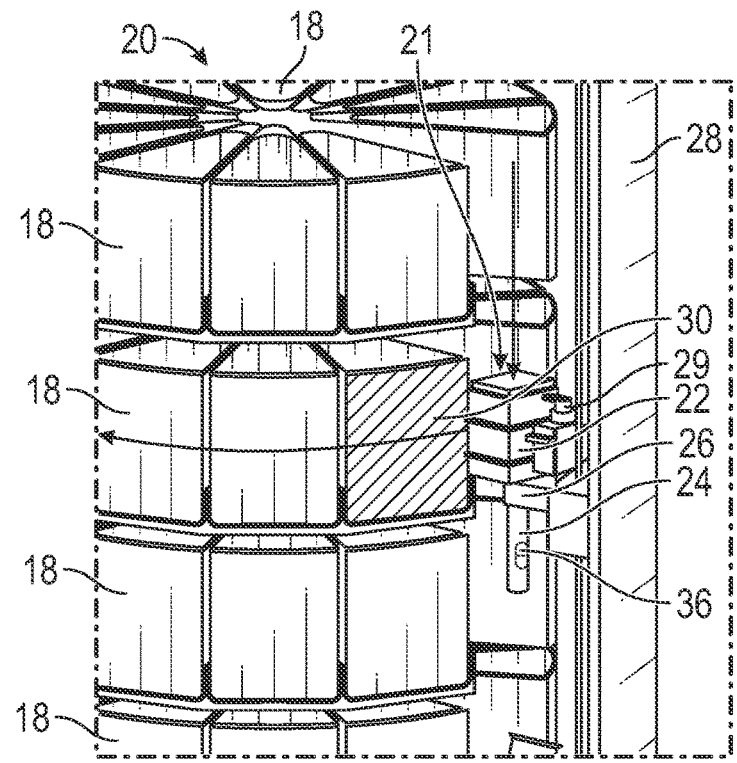
FIG. 7 is an enlarged front view of a portion of the medication dispenser and showing the extraction device extracting the medication from the compartment, constructed and operative in accordance with the present invention.
Figure 8:
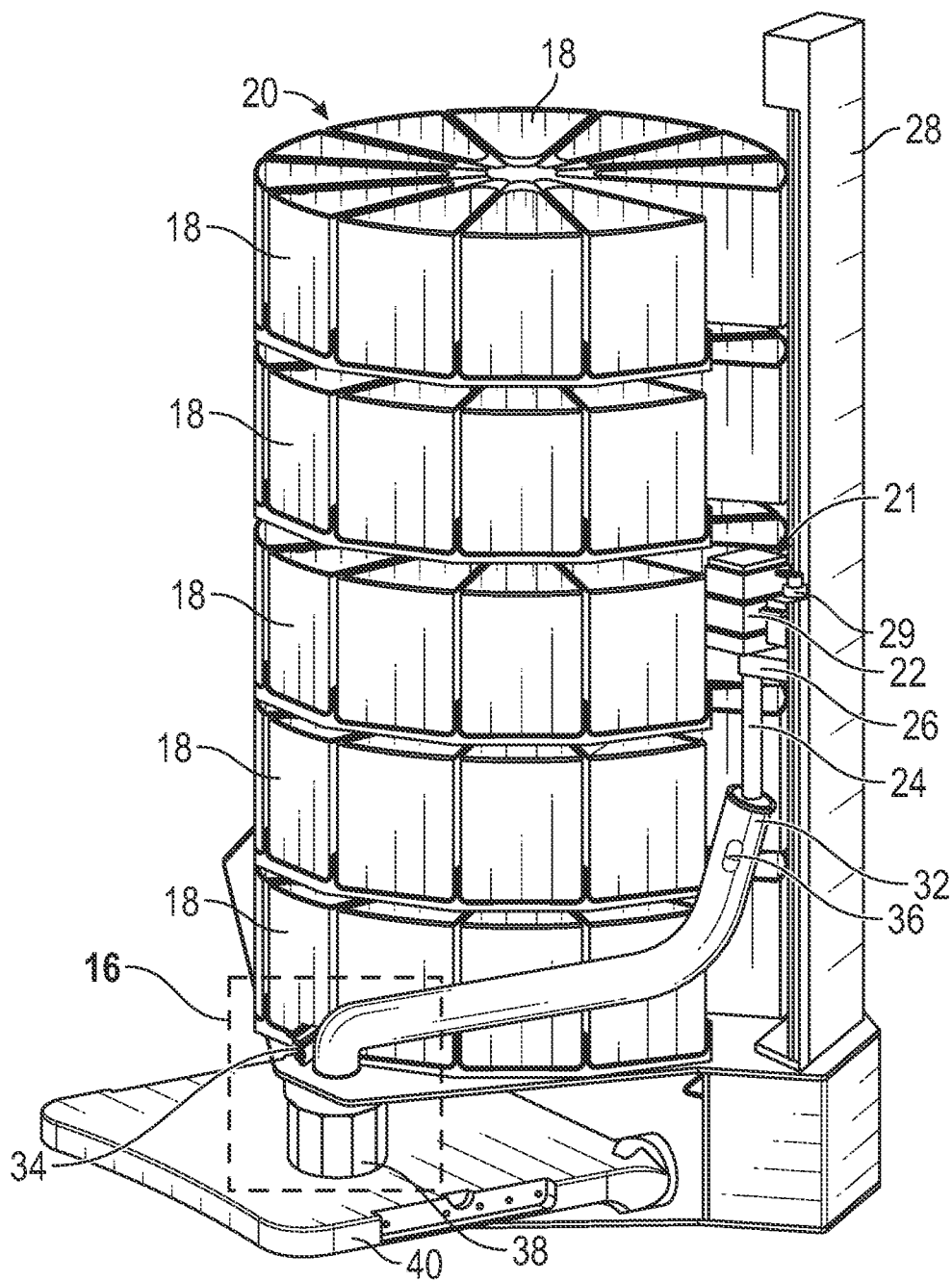
FIG. 8 is front perspective view of the medication dispenser and showing the extraction device traveling through the exit tube, constructed and operative in accordance with the present invention.

As seen in FIG. 5 to which reference is now made, carousel 20 rotates until compartment 30 is in vertical alignment with the vacuum tube 24. The extraction device 21 is lowered along rail 28 until the vacuum tube 24 engages the target compartment 30 as shown in FIG. 6 to which reference is now made. Then, the vacuum motor 29 is activated to create a vacuum and the medication is sucked into to the vacuum tube 24. Carousel 20 is rotated until the extraction device 21 is clear of the target compartment 30 and is contained within a clear column as shown in FIG. 7. Extraction device 21 is lowered until the vacuum tube 24 is in juxtaposition with the exit tube 32. As shown in FIG. 8, to which reference is now made, extraction device 21 is partially rotated until vacuum tube 24 aligns with the exit tube 32. Motor 29 is deactivated and vacuum pump 22 stops. This terminates the vacuum and the medication drops into exit tube 32.

Figure 9:
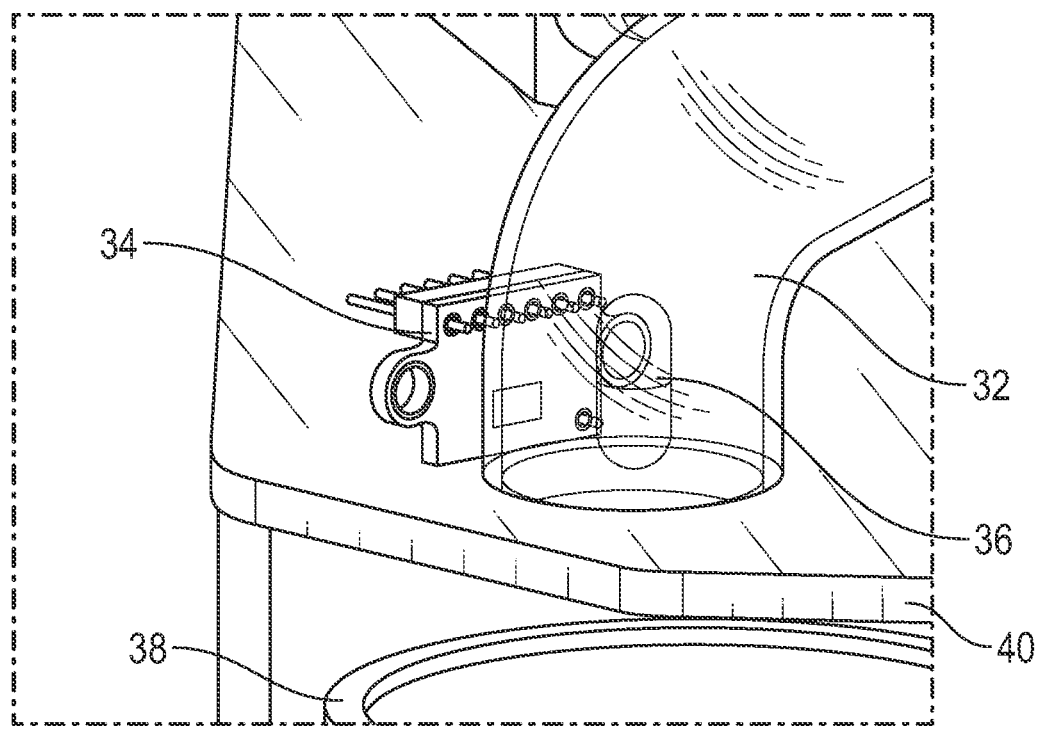
FIG. 9 is an enlarged front view of a portion of the medication dispenser and showing the exit tube with the composition sensor, constructed and operative in accordance with the present invention.

In a preferred embodiment, as shown in FIG. 9 to which reference is now made, near the bottom of exit tube 32, a composition sensor 34 may be positioned. As the medication 36 passes, sensor 34 scans it to determine its composition. The scan information is compared to the information about the target medication held in memory to ensure the correct medication for this individual was dispensed.

Figure 10:
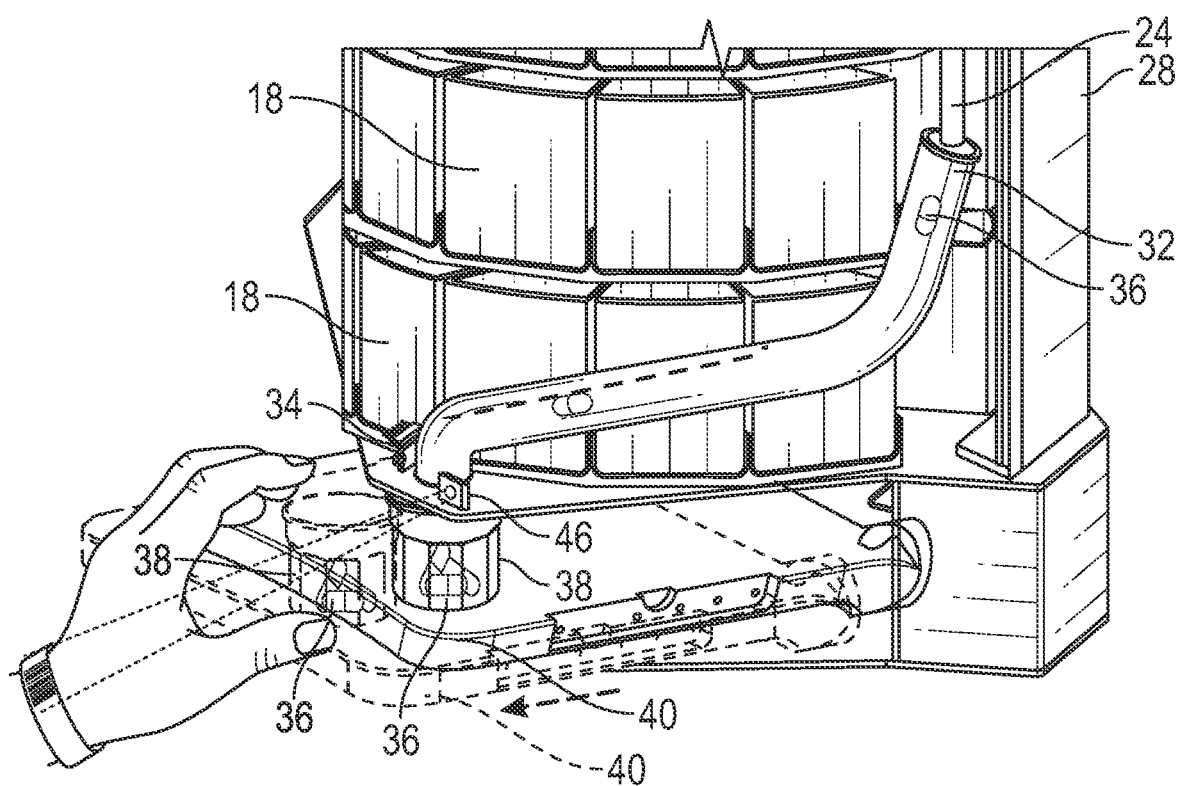
FIG. 10 is an enlarged front view of a portion of the medication dispenser and showing the medication dropping into a dispensing cup, constructed and operative in accordance with the present invention.

Thereafter the medication 36 drops into a cup 38 or another suitable receptacle as shown in FIG. 10 to which reference is now made. In a preferred embodiment, cup 38 is situated on a movable tray 40. To facilitate access to the cup with the medication the tray may slide out. When pushed all the way in, cup 38 aligns with the exit tube 32 to catch and retain the medication 36. For easy access, the tray can then be pulled out.

Figure 11:
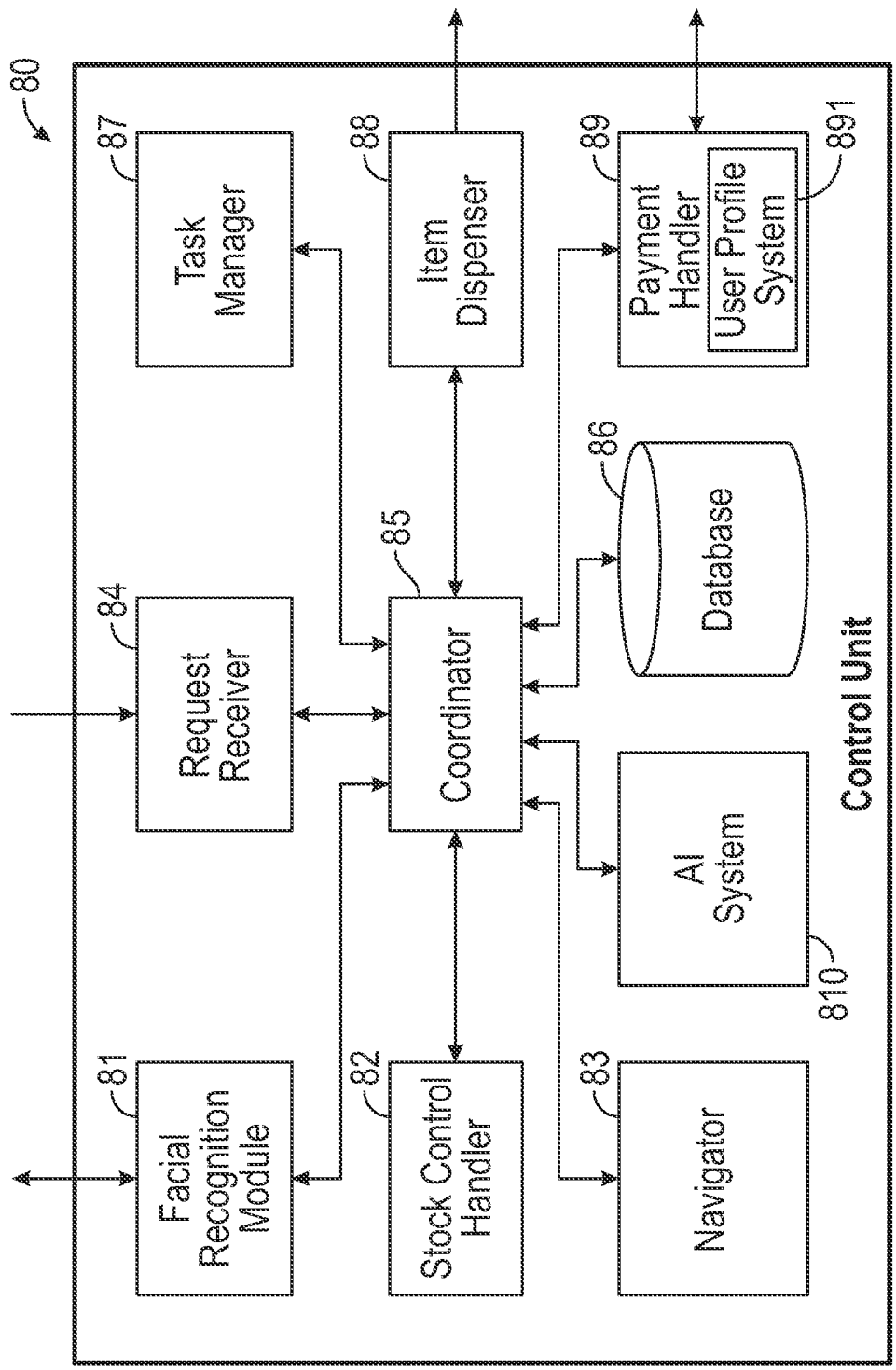
FIG. 11 is a schematic diagram of the elements of the control unit of FIG. 1, constructed and operative in accordance with the present invention.

Reference is now made to FIG. 11 which illustrates the sub elements of control unit 80 for controlling robot 2. Control unit 80 may comprise a facial recognition module 81, a stock control handler 82, a navigator 83, a request receiver 84, a coordinator 85, a memory module or database 86, a task manager 87, an item dispenser 88, a payment handler 89 and an AI (artificial intelligence) system 801. Coordinator 85 may coordinate between the different elements. The functionality of these elements is described in more detail herein below.

Facial recognition module 81 may receive facial input from scanners and compare them with optical recognitions held in a database 86 to identify a person. Stock control handler 82 may monitor the stock of items for distribution as held within robot 2, coordinator 85 may coordinate between the different elements of control unit 80. Database 86 may be an external or internal memory module electronically connected to robot 2 and may contain optical recognition scans and personal information of persons located within a premise together with substantive information of designated items. Task manager 87 may coordinate between requests made to robot 2, item dispenser 87 may control dispensing unit 200 according to the output of facial recognition module 81, payment handler 89 or stock control module 82. Payment handler 89 may receive direct payments or payment information made to robot 5 and may also instruct external payment services. AI (artificial intelligence) system 801 may provide artificial intelligent and decision making support for the elements of control unit 50. The functionality of the elements are discussed in more detail herein below.

Thus, control unit 80 may provide the means for autonomously moving robot 2, control of optical recognition scanners, and the means for dispensing. It will be appreciated that control unit 80 may direct the means for autonomously moving to move the robotic device within a premise (via navigator 83), direct optical recognition scanners 42 to scan persons as they are encountered, compare images from the optical recognition scanners to optical recognitions stored in database 86 and to identify a person (facial recognition module 81). Upon identifying a person, control unit 80 searches the personal information of the person in database 86 and identifies designated items specified for the person, and then directs the means for dispensing to dispense the designated item to the person (via item dispenser 88).

As an additional safeguard, robot 2 may comprise a secondary recognition scanner and may store secondary recognition scans of persons located within a premise. Prior to dispensing the designated item, control unit 80 may direct the secondary recognition scanners to scan the person, compare images from the secondary recognition scanners to secondary scans in the database 86 to confirm the person is the correct person to receive the designated item. In some embodiments, optical recognition scanner 42 can also be used as the secondary recognition scanner.

Figure 12:
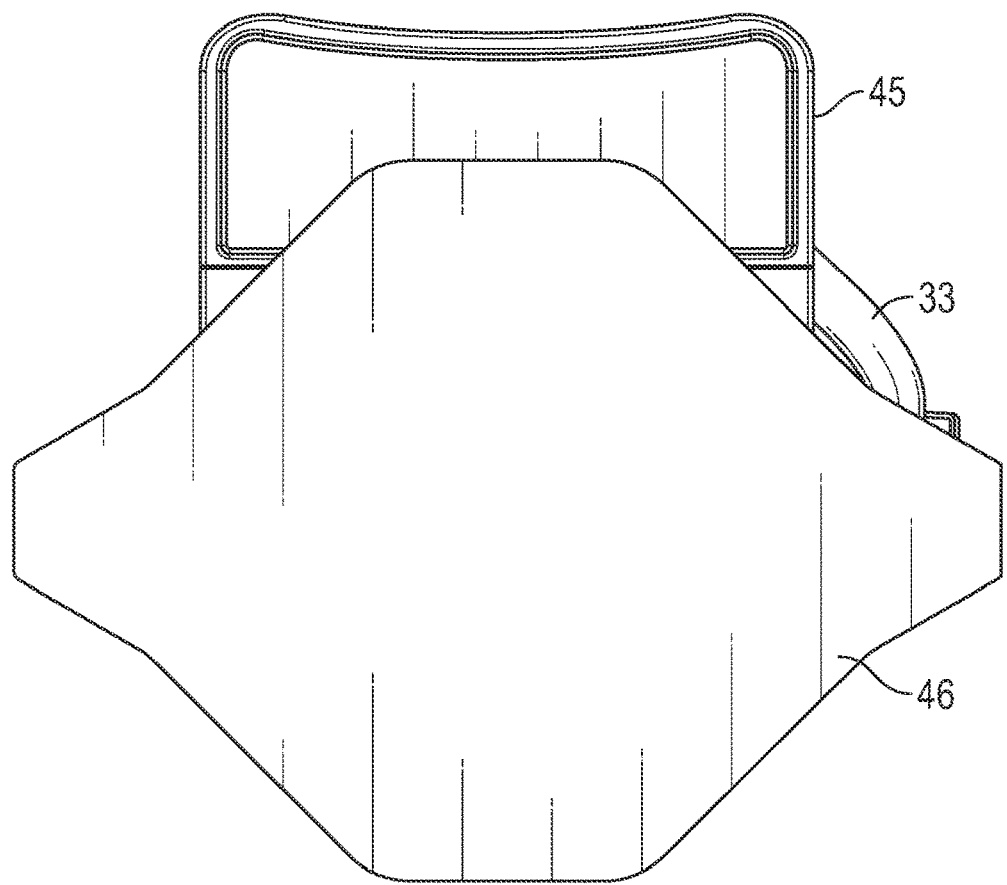
FIG. 12 is a scanner reading a magnetic code on a wrist band of a recipient of medication constructed and operative in accordance with the present invention.

It will be appreciated that in this manner, the correct person receives the correct medication. Serious medical consequences, and even death, can occur if a person gets the wrong medication. Accordingly, in a preferred embodiment, an additional scanner is provided by exit tube 32. In this manner, robot 2 may confirm that the person receiving the medication is in fact the correct person. Instead of optical scanners 42 and 46, other scanners may be used, such as eye scanners, fingerprint scanners, facial scanners, and other technology. Reference is now made to FIG. 12 which shows scanner 46 reading a magnetic code 45 on a wrist band 33 of the recipient of the medication.

Therefore, in a preferred embodiment, secondary recognition scanners may be magnetic code readers, facial scanners or fingerprint scanners or eye scanners or optical scanners and said secondary recognition scans of persons located within said memory may be magnetic codes, fingerprint scans or eye scans or facial scans or optical scans. In some embodiments, the optical recognition scanners 42 can also be used.

Another important aspect is to make sure the correct medication is selected. Therefore, it is important to double check to make sure the correct medication is in the dispenser. For this purpose, scanners are affixed to the dispenser. Prior to vacuum tube 24 removing the designated item, a scanner may scan the item to confirm its substance. In the marketplace, there are any number of scanners that can determine the composition and make up of a medication.

Therefore, preferably, the means for dispensing further comprises substantive scanners 48 (FIG. 6) and database 86 further contains substantive scans of said designated items; and, where, prior to dispensing the designated item, control unit 80 directs the substantive scanners to scan the designated item, compares scans from the substantive scanners to substantive scans in the memory to confirm the designated item is the correct designated item for the person.

Still another safety implementation is to include still another scanning system to be used when the dispenser is filled in order to make sure an authorized person is filling the dispenser. This helps to ensure that the correct medication is in the correct compartment. Depending on the configuration of the robot, optical recognition scanner 42 or additional optical scanner 46 may be used, or still another scanner can be implemented on robot 2. It may be appreciated that the specific location of the additional scanner is dependent on the specific configuration of robot 2. The only limitation is that it must necessarily have a clear sight line to the person requiring the medication.

Therefore, preferably, the storage means further comprising supplemental recognition scanners; and database 86 further containing supplemental recognition scans of persons authorized to add items to the storage means; and, where, prior to adding items to the storage means, control unit 80 directs the supplemental scanners to scan persons attempting to add items to the storage means, compares scans from the supplemental scanners to supplemental scans in the memory to confirm the persons attempting to add items to the storage means are authorized to add items to the storage means.

Figure 13:
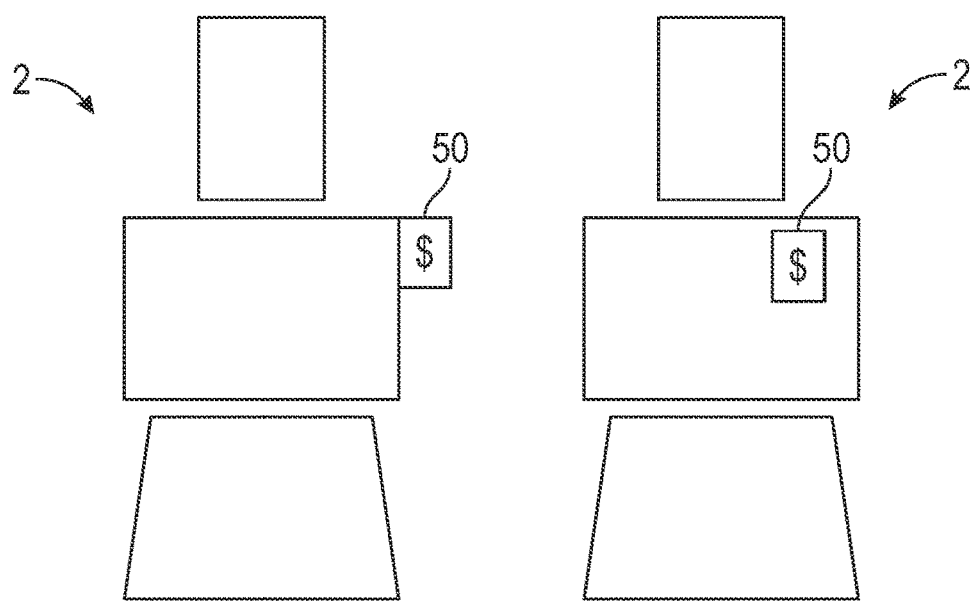
FIG. 13 is a front view of the robot of FIG. 1 showing positions of coupled payment terminals, constructed and operative in accordance with the present invention.

As discussed herein above, the dispensing capabilities of robot 2 may be used as part of a vending machine/delivery system. In an alternate embodiment to the present invention, robot 2 may further comprise a payment terminal 50 embodied with robot 2 as is illustrated in FIG. 13 to which reference is now made. Payment terminal 50 may process payment of a user purchasing an item from robot 2 and may include but not be limited to traditional credit and debit card processing, contactless payment, and QR code scanning. Any known payment terminal or point of sale terminal known in the art may be used. Payment terminal 50 may operate over a wired connection like USB or ethernet or a wireless connection like a cellular network, Bluetooth, or Wi-Fi. payment may additionally be verified via payment handler 89 with the use of facial recognition, location data, image recognition, or known user data. Payment terminal 50 may be a card reader, NFC (near field communication) reader, or any known means of payment reception. Payment handler 89 may comprise a user profile system 891 which may allow for payment to be automatically charged to a recipient's room. This can be achieved via any user identification method, including scanning of a room key, scanning of a QR code on a mobile phone, NFC or Wi-Fi transfer from a mobile phone, or facial recognition via facial recognition module 81.

Payment terminal 50 may be embodied at a location convenient for the use of a standing adult human. An example of this is at the robot's shoulder height along the torso or integrated into the torso, as shown in FIG. 13 back to which reference is now made. The communication of data between robot 2 and payment terminal 50 may be handled via payment handler 89 via code, application, software, or drivers to communicate with payment terminal 50.

Figure 14:
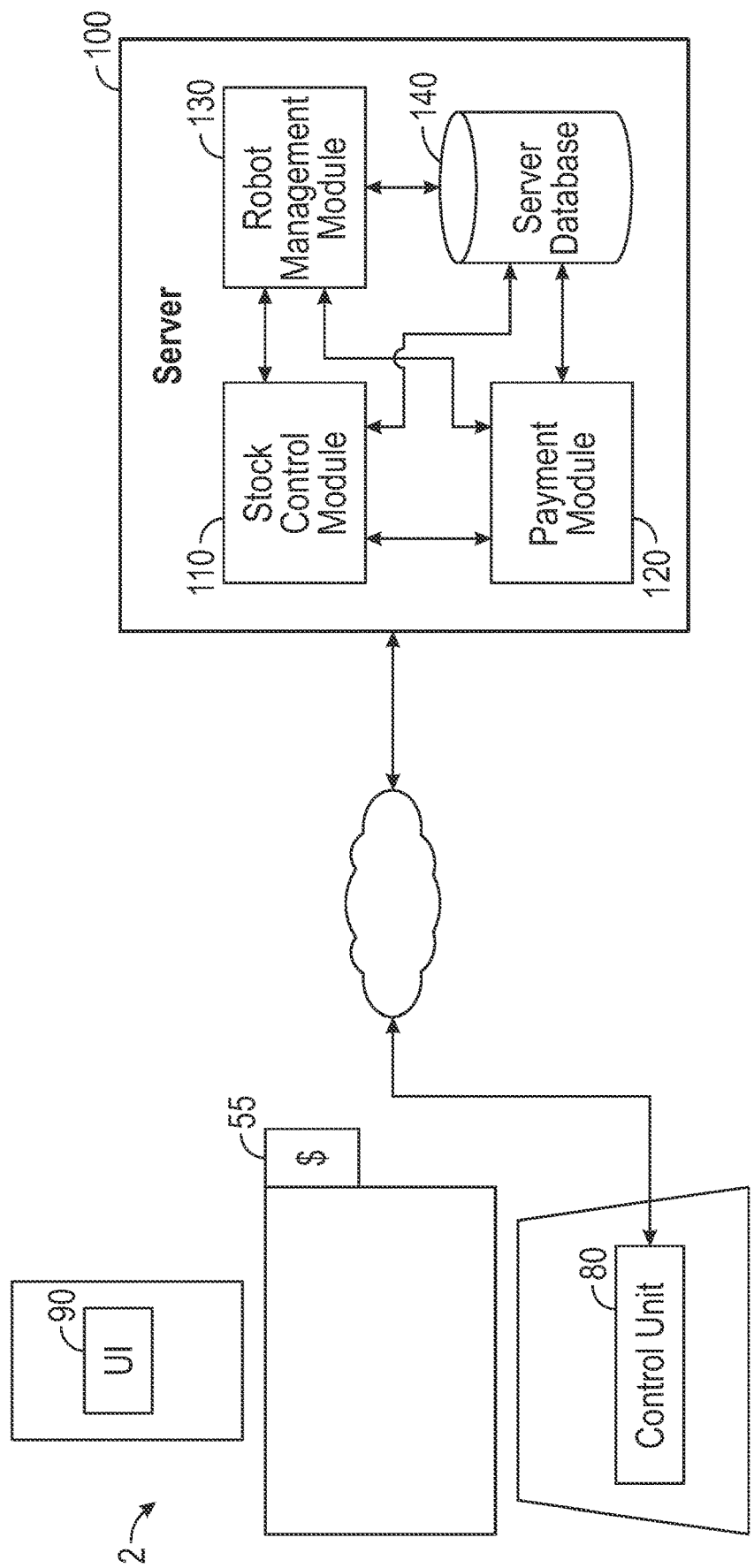
FIG. 14 is a schematic illustration of the robot of FIG. 1 in communication with an external server, constructed and operative in accordance with the present invention.

In yet another embodiment, for example, if a user is a guest at a hotel the user's billing information or invoicing information may already be known and charged to the room. In this scenario, robot 2 may be in communication with an external server 100 such as the hotel management/payment system as is illustrated in FIG. 14 to which reference is now made. The user location data and image recognition (images taken of guests at check-in for example) may verify the room location and room number, respectively. The user may also be recognized through facial recognition if the data is known to the robot or server coupled to the robot already. Accordingly, any additional charges may be added to the room cost. In this scenario, server 100 may comprise a stock control module 110, a payment module, a robot management module 130 and a server database 140 which may communicate with control unit 80 and are described in more detail herein below.

As discussed herein above, the presence of mobile vending robot 2 may alleviate the need for full-time staff on each floor of (as an example) a hotel. This allows each staff member to accomplish more in managing amenities, refills, and restocks with greater ease. Such a robot can go to each guest or room individually and keep a direct account of its inventory. Keeping direct account of the inventory in combination with autonomous movement allows the robot to know when a refill is required and return to a restock room when it is required. Therefore, the staff will have a singular point of operation (possibly per floor or with the use of smart elevators per building or complex) and not need to run around, and they can be notified when they must perform a task.

It will be appreciated that robot 2 may have a vending machine mode where it distributes items for payment or a delivery mode where it delivers pre-determined items.

Figure 15:
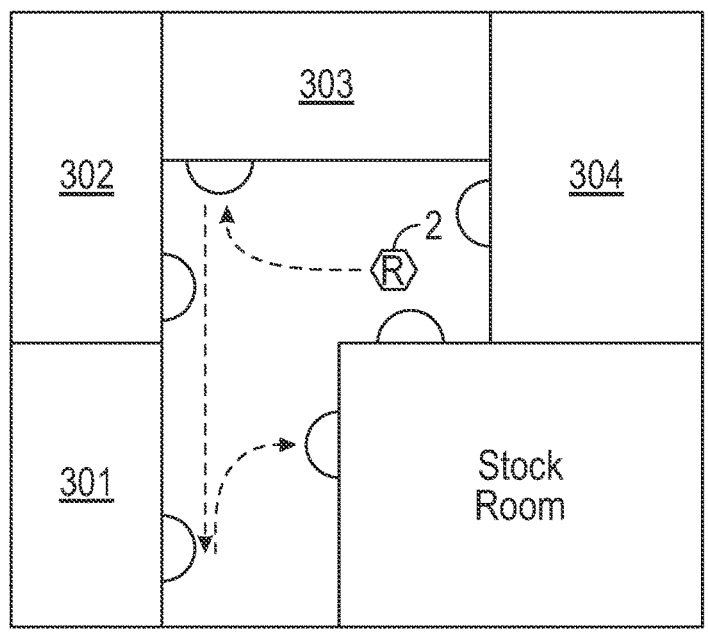
FIG. 15 is a schematic illustration of the robot of FIG. 1 servicing multiple rooms of a hotel floor, constructed and operative in accordance with the present invention.

Reference is now made to FIG. 15, which illustrates robot 2 as a delivery robot for a floor of the above mentioned hotel scenario. In this example, robot 2 receives a call from guests in rooms 303 and 301. The calls may be in the order of room 303 then room 301. In this scenario request receiver 84 may receive the 2 requests and task manager 87 may determine which order to handle the requests. It will be appreciated that the requests may be concurrent or within a pre-defined time period. In an alternative scenario the rooms may be hospital rooms or any similar type of commercial establishment. It will be appreciated that requests may come via a GUI on robot 2 (as discussed in more detail herein below), or from an external source such as server 100).

Robot 2 arrives (as an example) to room 301 and receives the request for items from the guest. If the items are in stock, they are delivered. Robot 2 may then add the request to the list of items robot 2 will need to stock up on for future deliveries. Robot 2 may then travel to the stockroom where the responsible staff member will receive a list of the required items from robot 2, the items required for each room, or both, and restock robot 2 accordingly. Robot 2 may then navigate to the rooms to deliver the items to the users in rooms 301 and 303. It will be appreciated that task manager 87 may control robot 2 based on time since delivery request, FIFO (first in first out), closest room first, the shortest distance to travel, or any appropriate means to determine optimal delivery times.

It will be appreciated that at any point robot 2 may be triggered to restock or reposition itself by stock control handler 82 which may keep track of any stock held as discussed in more detail herein below. This trigger may be for example, a request from a server, an item running out or low, historical data indicating a good time to restock without loss of function for users, historical data indicating a surge in use by users in a short while, a set amount of time passing, a set time passing, or any appropriate trigger to benefit the use of the robot for the users or to the profits of the vending machine.

Robot 2 may have two main modes, stationary vending machine mode, and mobile delivery mode. Robot 2 may be optimized for specific mode use or optimized for switch mode use or a combination of both.

Figure 16:
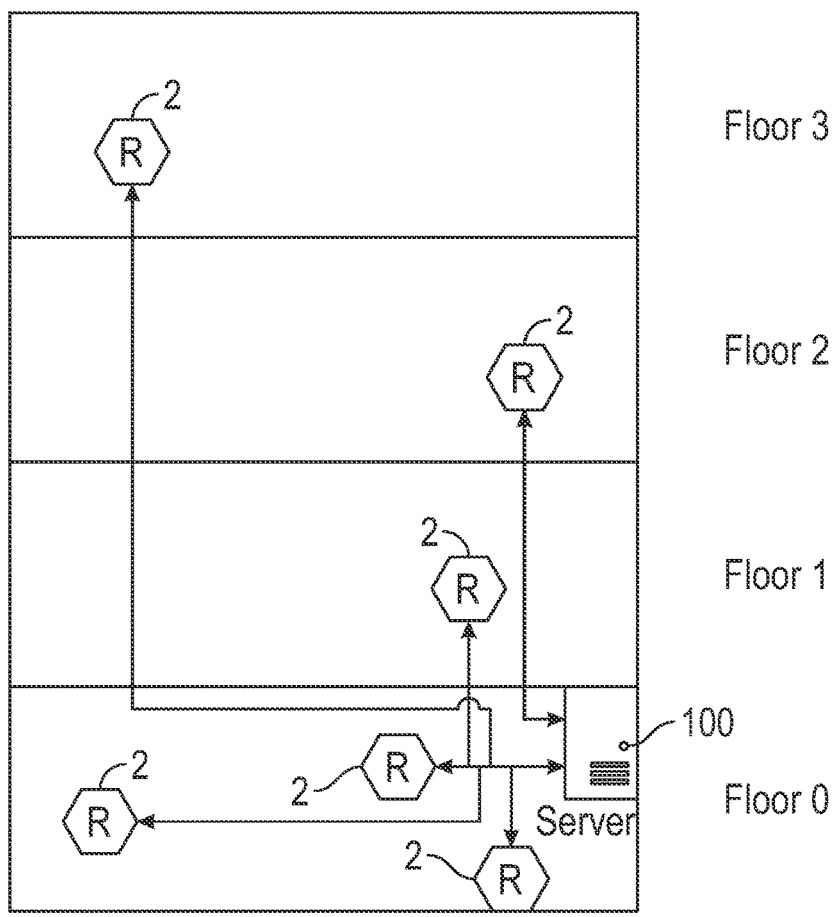
FIG. 16 is a schematic illustration of multiple robots servicing a multi-story building, constructed and operative in accordance with the present invention.

Reference is now made to FIG. 16, which shows the use of multiple robots 2 operating throughout a complex distributed on different floors of an establishment such as a hotel. In this example, each robot 2 may be in vending machine mode or in delivery mode. Each robot 2 may be designated to a floor or designated to an area. The locations may also overlap. For example, on floor 0 there may be several robots in an area that may have more foot traffic such as a hotel lobby. Each robot 2 may be coupled wirelessly to server 100 as is illustrated in FIG. 14 back to which reference is now made. In this scenario, robot management module 130 may coordinate multiple robots 2 accordingly.

The connection to server 100 may be through the use of an internet or intranet connection. Server 100 may be a local server for the storage and communication of the requested items, the items in stock, rooms in a queue, when to restock data, historical data of uses, operations, requests, and purchases of the robot, and the items, or log of transactions, a dictation by the staff to the robot to operate in accordance with the staff needs, etc. Robot management module 130 may allow the robots to communicate and coordinate with one another to ensure no overlap in designated tasks.

For example, server 100 may designate three delivery robots 2 for floor 0 with one robot stationery and two mobile. To ensure that all three delivery robots 2 do not duplicate orders and deliveries to users, robot management unit 130 may coordinate between the robots 2 to avoid any conflicts. This may apply to any number of robots 2, mobile or stationary robots. For example, if a user places an order to a mobile or stationary robot 2 that is not holding the required item, robot management module 130 may instruct stock control module 110 to add it to the order list for the particular robot 2. If the user then approaches a second robot 2, the second robot 2 may recognize the user and robot management module 130 may instruct the secondary robot 2 to automatically dispense the item or items that were out of stock in the first robot. Robot management module 130 may then remove the order from the order list of the first robot 2.

Server 100 may also be in communication with and control of the staff and concierge to ensure that staff properly set up the restocking room for restocking robot 2 such as instructions to place "x" number of products on shelf "y". It will be appreciated that the restocking staff may also communicate with robot 2 via a mobile app, desktop app, tablet or any other communication device in lieu of or addition to GUI 90.

Just like regular vending machines, robot 2 may have many different storage arrangements depending on the needs that are being served or the items being dispensed. It will be appreciated that storage compartments 18 may differ in shape and number to be adjustable to fit a variety of item sizes.

Figure 17:
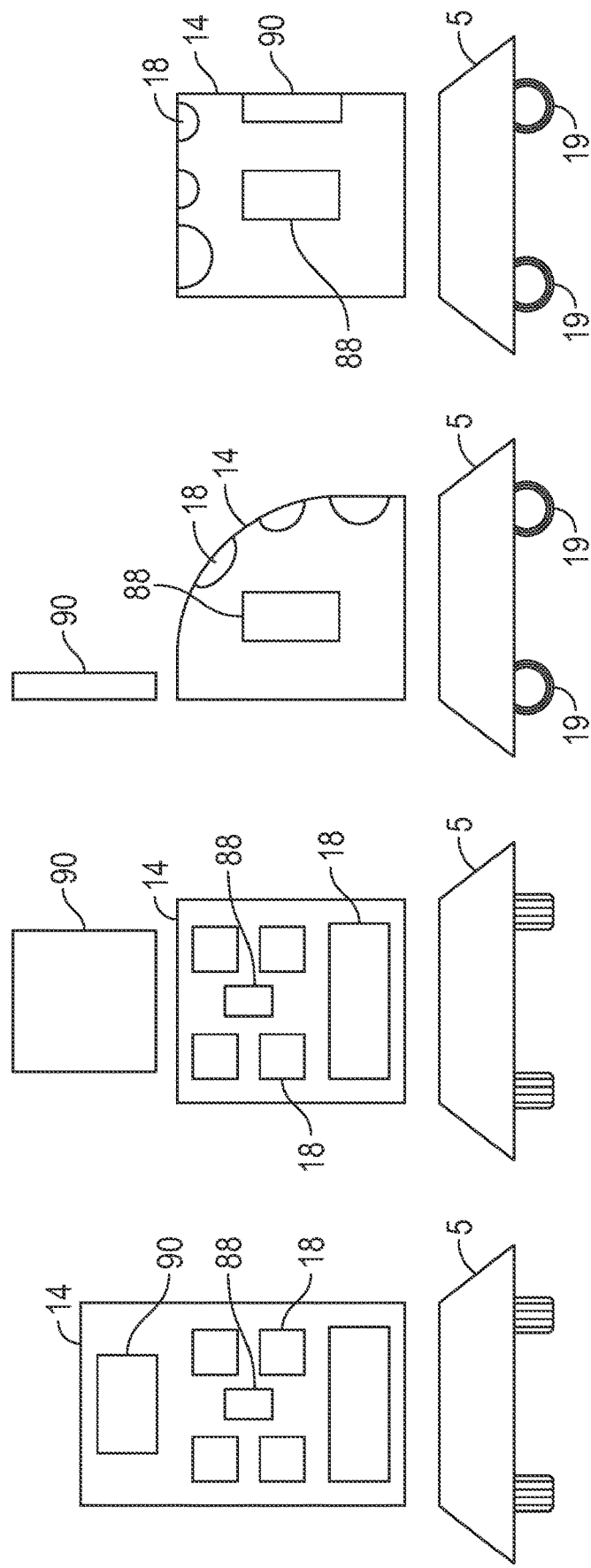
FIGS. 17A, 17B, 17C and 17D show alternate designs for a robot vending machine, constructed and operative in accordance with the present invention.

Reference is now made to FIGS. 17A-D, which illustrate several designs for robot 2 comprising a base 5 and wheels 19 for autonomous movement, a dispenser 88 between base 2 and a torso 14 comprising compartments 18 of assorted sizes, and a user interface 90. UI 90 may also be a separate module as seen in FIGS. 17B and 17C. In a specific example where robot 2 has items for purchase, the torso 14 or a separate module may comprise a payment terminal 50 and may further comprise an internal printer for receipts. In a specific example of a robot 2 carrying items for distribution to hotel guests, large compartment 18 may be filled with frequently accessed items that may be universally accessible, and small compartments 18 may comprise less common or more specific ordered items retrievable only to an individual who is the designated recipient of said items. As seen in FIGS. 17A-D, the shape of torso 14 may vary each with an alternative means of providing item retrieval and UI 90 may be positioned for access ease for a user.

It will be appreciated that robot 2 may use intelligence and AI via AI system 810 to learn when is the most appropriate time to restock items based on the current levels of items in stock, the historical or static data on the demand of the items in stock, the historical or static downtime the robot experiences at the moment in time, and the availability of a responsible staff member to be able to refill the items, or any other beneficial data to efficiently restock items. This may be amplified by the robot's ability to communicate with other items dispensing robots and their data as well cumulatively.

Stock control handler 82 may implement a restocking algorithm that can optimize restocking efficiency based on commonly used algorithms like Economic Order Quantity (EOQ) or use proprietary algorithms based on AI and historical data stored in database 86.

In addition, robot 2 may use its autonomous moment feature to navigate (using navigator 83) to a more centralized restock room location where a responsible staff member will appropriately restock, refill, clean, replace, check the expiration date, and know the quantity on hand of stored items. The use of stock control handler 82 may help aid the responsible staff member by keeping track of things like quantity on hand, expiration dates, times when cleaning must occur, etc.

It will be appreciated that robot 2 may additionally provide modules that comprise a means of keeping items fresh and unspoiled using refrigeration, heating, and general temperature controls. It may also employ the use of humidity controls, control of light exposure, and general cleanliness using for example air filters.

In an alternative embodiment, robot 2 may employ a recipient verification system. In the example of a robot distributing items, the verification may be tied down to a location, such as in front of a door for a specific room number verifying the recipient as the guest in said room, a room card or key, credit or debit card, a passcode, etc. In a scenario where robot 2 is more stationary and distributing simple items, a credit or debit card or room key card may be used if verification is required.

This may be useful in the case of payments of items for purchase or payment of lost items for borrowing as an item will be associated with the guest via credit or debit card or room key card. The credit or debit card can be paid for directly and the room key card can be charged to the room.

This process can be used for example for the delivery of standard goods requested from hotel attendees, for example, soap, towels, etc., or individual requests like room service, etc.

Figure 18:
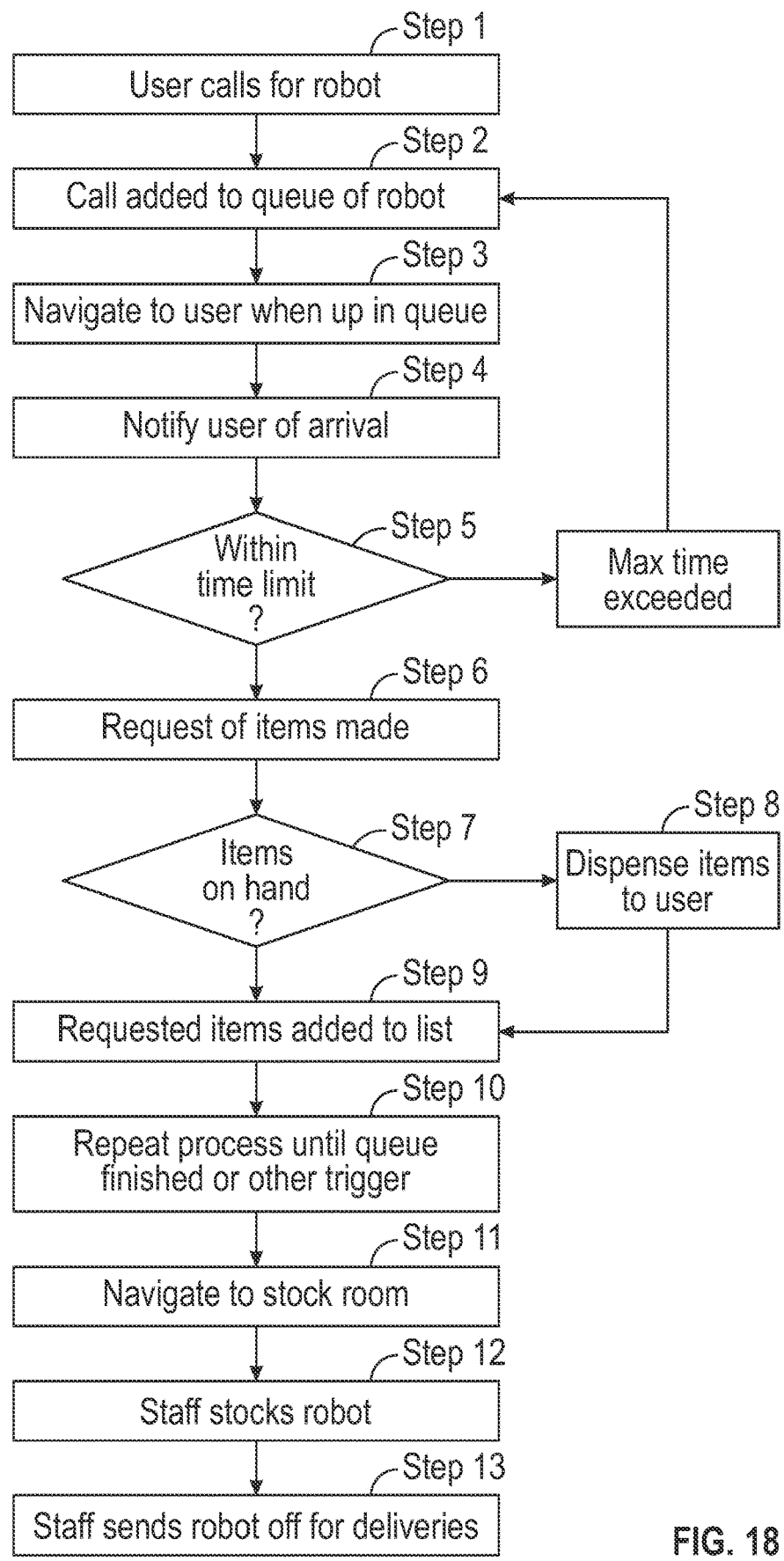
FIG. 18 is a flowchart showing the flow of functionality for a hotel guest requesting a delivery from a robot, constructed and operative in accordance with the present invention.

Reference is now made to FIG. 18 which illustrates the flow of process for the hotel guest requesting a delivery. The user or guest may summon robot 2 (step 1). In one method each room may comprise a call service button like that on an airplane. Once pressed a robot will add the requested visit to a queue log (step 2) which can be handled by task manger 87.

After receiving the request via request receiver 84 (which may come via UI 90 or from server 100), robot 2 may proceed to the room with navigation with the help of navigator 83 (step 3) and notify the requester that it is ready and waiting at the door (step 4). The notification may be verbal or use the call service button for notifying the guest.

The robot may have an internal clock measured against a minimum wait time and/or a maximum wait time so the robot does not wait forever, nor does the requester miss his opportunity to get to the door. If the user does not show up in the allotted time the robot may leave and drop the request (step 5) or go back to step 2 and place the request back in the queue log. In an alternative embodiment, the phone line to a reception/concierge can be used to initiate the request through a person whose message is delivered to the robot through them. In this example robot 2 may proceed to step 6.

If items are readily available (step 7), robot 2 may give over the requested items and finish the task (step 8).

It will be appreciated that the user requesting items from robot 2 may request 1 or more items. For each item, if the item is readily available (step 7) the robot 2 may give over the requested item. If the item is not available (step 9), robot 2 will add the item to requested items list. It will be appreciated that robot 2 may hold a list of the required items for fetching associated with the room number for tracking and that robot 2 may visit multiple rooms in the call queue following the steps above. This may be until the call queue is completed or until a threshold is reached, for example, the number of requests exceeds a certain amount or the number for requested items exceeds a certain amount (step 10).

Robot 2 may then navigate to a more centralized stock room (step 11) where a responsible staff member will gather the requested items and place them in the robot for delivery.

The responsible staff member may interact with the robot UI or separately be aware of the orders via a request system through a mobile app or computer (step 12). Robot 2 may also identify and verify the staff member using facial recognition module 81. Additionally, the responsible staff member may associate a specific compartment to the specific requester as seen in robot build and design and recipient verification.

If an item is unavailable, there may be an "out of stock" option, and a notification may be sent to the guest via GUI 90 that an ordered item cannot be fulfilled at the current time.

When the responsible staff member has stocked up the requests, they may press, for example, a GO button on UI 90 or any device in communication with the server coupled to robot 2 to send the robot to deliver the items (step 13) to the pertinent guests.

Figure 19:
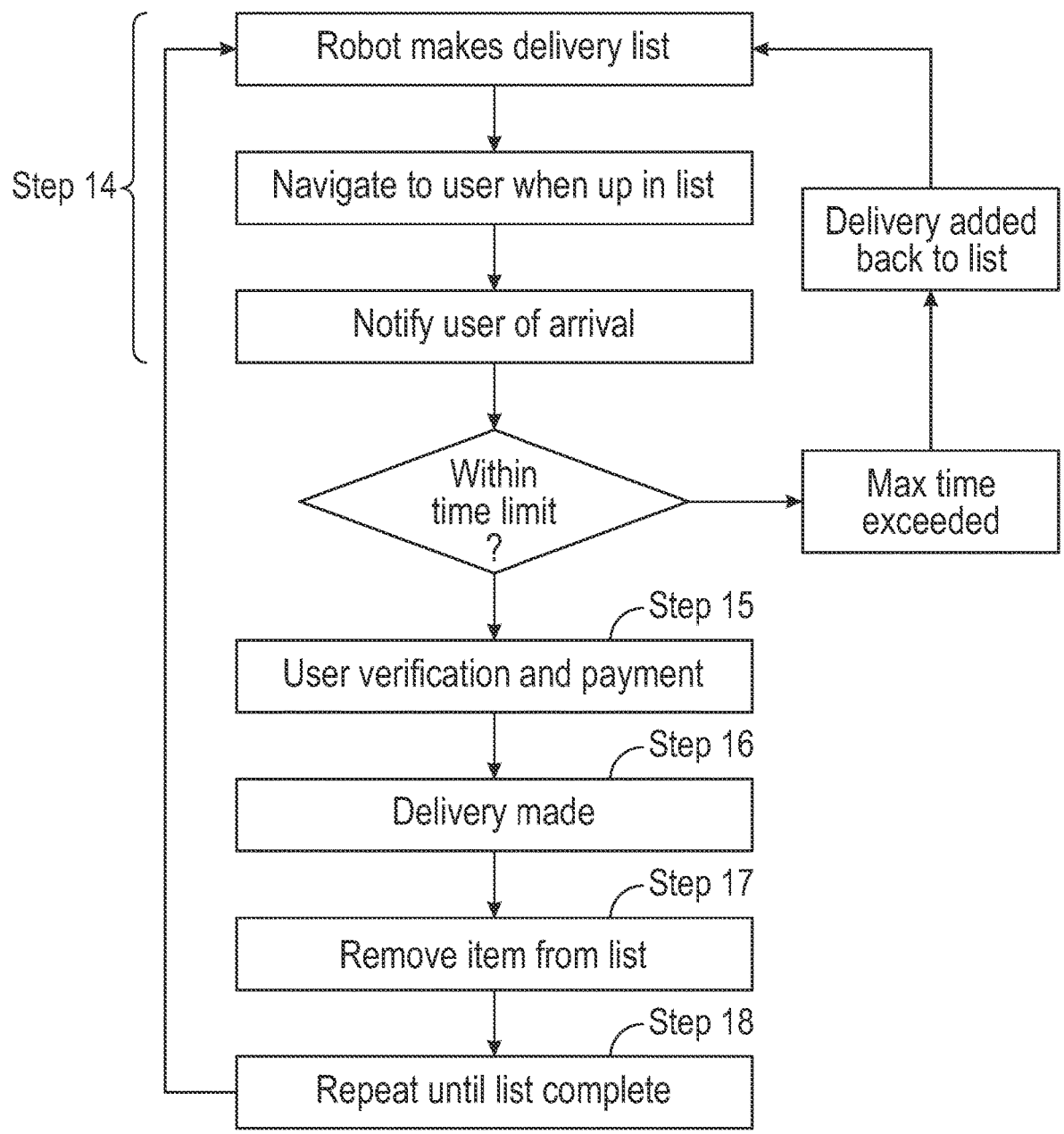
FIG. 19 is a flowchart showing the flow of functionality of the vending machine mode, constructed and operative in accordance with the present invention.

Reference is now made to FIG. 19 which shows the functionality of the vending machine mode. It will be appreciated that when in vending mode, robot 2 may create an order list (via task manager 87), navigate to the user/customer and notify them of its arrival (step 14). It will be appreciated that robot 2 may then wait an allotted time for the customer to respond in a similar manner to step 5 as described herein above. If the maximum time is exceeded, the delivery item may be added back to the delivery list. In this scenario robot 2, may start the process again and repeat step 14 for the next item on its list. Once a user responds to the robot's arrival notification, robot 2 may request payment via a payment method before the dispensing of the items. In this scenario, at step 15, payment handler 89 may handle any verification of payment and instruct item dispenser 88 to dispense the item or items accordingly. Once an item is dispensed and delivered (step 16), it may be removed from the robot's delivery list (step 17). This process is repeated until the delivery list is completed or any other appropriate trigger stops the process (step 18).

It will be appreciated that there may be various sub modes when robot 2 is in stationed mode i.e. robot 2 operates at a station in a static matter which may be distributing simple goods. Sub-modes may include standard station mode, a singular place where the robot is stationed, rotating station mode: multiple stations shifted in rotation, and dynamic station mode: multiple stations shifted dynamically.

As discussed herein above stock control handler 82 may maintain stock control, and may determine when all or most items run low or run out, when several items run low or run out, when an item runs low or runs out, when a frequently selected item is running out or running low, when 1+low-frequency item(s) are running out or running low or when a refill is determined to be required.

The exact dispensing method to optimize the useability for the user may vary. For example, any standard vending machine dispenser known in the art, a simple compartment with a latch openable by the verified recipient of the items. They may be any standard vending machine dispenser known in the art (including vacuum systems, grid-like pickup systems, gravity systems, etc.), or a simple compartment with a latch openable by the verified recipient of the items. When operating with recipient verification, the latch would only be openable by a verified recipient. Other variations to the dispenser may be possible as well depending on the nature of the items being delivered. For example, if robot 2 is delivering hot food, it may have a heated compartment or a cold compartment for cold food. Robot 2 may not be limited to any single dispenser method but may include any combination of the above possibilities.

As discussed herein above, robot 2 may comprise a user interface 90 for user interactions with robot 2. This can be as simple as a keypad for selecting an item to dispense or typing a passcode into commonly found on vending machines to a full screen with selection menus and telepresence to a concierge. For the more complex UI 90, UI 90 may provide a selection screen of items to take or to order, notifications of for example room information and updates, if items are out of stock, allow guests to make changes to check in/out status or do not disturb status, etc., telepresence to a concierge or required staff, or provide general user interaction like text-to-speech (TTS) etc.

Hotel staff may also find UI 90 beneficial to receive and update data about, for example, what orders have been fulfilled and ready for distribution or delivery, what compartment the orders are in, what items are out of stock and unable to be fulfilled, if cleaning is required or was done, item expiration dates to be set or gotten rid of, a control system for more nuanced needs of the robot's operation (example from fetch quest: force send or prioritize or route robot deliveries).

It will be appreciated that robot 2 may store this data in database 86 and using AI system 810 maximize the efficiency of its tasks and the ability to share information with other dispensing robots 2.

This may include maximizing customer satisfaction, profits, tasks completed, average task time, least downtime, etc. This may further comprise but is not limited to the current levels of items in stock, the historical or static data on the demand for the items in stock, the historical or static downtime the robot experiences at the moment in time, and the availability of a responsible staff member to be able to refill the items, or any other beneficial data to maximize efficiency.

Using this intelligence, robot 2 may also build a historical database within database 86 to optimize future efficiency.

This may further comprise the optimization of deliveries by maximizing the efficiency of routes and queued tasks. For example, shortest route, fastest route, FIFO, etc. This may also take into account a task active state which can be true or false depending on if the robot is currently carrying out a task at the moment or not.

Some general-purpose computers may comprise at least one communication element to enable communication with a data network and/or a mobile communications network.

Unless specifically stated otherwise, as apparent from the preceding discussions, it is appreciated that, throughout the specification, discussions utilizing terms such as "processing," "computing," "calculating," "determining," or the like, refer to the action and/or processes of a general purpose computer of any type, such as a client/server system, mobile computing devices, smart appliances, cloud computing units or similar electronic computing devices that manipulate and/or transform data within the computing system's registers and/or memories into other data within the computing system's memories, registers or other such information storage, transmission or display devices.

Embodiments of the present invention may include apparatus for performing the operations herein. This apparatus may be specially constructed for the desired purposes, or it may comprise a computing device or system typically having at least one processor and at least one memory, selectively activated or reconfigured by a computer program stored in the computer. The resultant apparatus when instructed by software may turn the general purpose computer into inventive elements as discussed herein. The instructions may define the inventive device in operation with the computer platform for which it is desired. Such a computer program may be stored in a computer readable storage medium, such as, but not limited to, any type of disk, including optical disks, magnetic-optical disks, read-only memories (ROMs), volatile and non-volatile memories, random access memories (RAMs), electrically programmable read-only memories (EPROMs), electrically erasable and programmable read only memories (EEPROMs), magnetic or optical cards, Flash memory, disk-on-key or any other type of media suitable for storing electronic instructions and capable of being coupled to a computer system bus. The computer readable storage medium may also be implemented in cloud storage.

The processes and displays presented herein are not inherently related to any particular computer or other apparatus. Various general-purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the invention as described herein.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

We claim:

1. A robotic device for distributing items, comprising:
   one or more storage compartments each capable of storing a designated item to be distributed;
   electronic memory storage operable to store information corresponding to one or more intended recipients of one of said designated items and information corresponding to each of said designated items and further operable to store payment information corresponding to at least one intended recipient;
   an electronic scanning device operable to scan and obtain payment information from said intended recipient and also operable to scan and obtain image information of said intended recipient;
   a control unit operably connected with said electronic memory storage and said electronic scanning device, and further operable to compare the obtained payment information of the intended recipient, the control unit further operable to compare the obtained image information of said recipient with the stored information of the intended recipient; and
   a dispensing unit operable to dispense a designated item to an intended recipient of said designated item after said control unit identifies the recipient and authorizes the dispensing of the designated item when the obtained payment information matches the stored payment information when the obtained image information of said recipient matches the stored information of said intended recipient and when the obtained image information of said recipient identifies the intended recipient as matching the stored payment information;

wherein the electronic scanning device is operable to obtain information corresponding to the item to be dispensed, and the control unit is further capable of authorizing the dispensing of the designated item when the stored designated item information matches the scanned designated item information.

2. The robotic device of claim 1, further comprising a motion unit capable of moving the robotic device.

3. The robotic device of claim 2, wherein the motion unit is capable of providing autonomous motion of the robotic device.

4. The robotic device of claim 1, wherein the electronic scanning device is operable to provide optical scans, magnetic codes, fingerprint scans, eye scans, and facial scans.

5. The robotic device of claim 4, wherein the stored intended recipient information comprises an image of the intended recipient and the electronic scanning device is operable to obtain an image of an intended recipient in a vicinity of the robotic device.

6. The robotic device of claim 1, wherein the electronic memory storage memory is internal to said robotic device.

7. The robotic device of claim 1, wherein the electronic memory storage is external to said robotic device.

8. The robotic device of claim 4, wherein the electronic memory storage is operable to store information corresponding to one or more individuals authorized to load one or more items into one of said storage compartments, and wherein the electronic scanning device is operable to obtain information corresponding to an individual attempting to load one or more items, and wherein the control unit is further operable to authorize the loading of one or more items when the stored individual authorized loading information matches the scanned individual loading information.

9. The robotic device of claim 1, wherein the item to be distributed corresponds to a pharmaceutical or medical product.

10. The robotic device of claim 1, wherein the control unit is further operable to determine when the restock the one or more items to be distributed.

11. The robotic device of claim 2, wherein the robotic device is operable to deliver said designated item to a specific designated recipient at a remote location.

12. The robotic device of claim 1, wherein the robotic devices are capable of communicating with each other.

* * * * *